United States Patent [19]
Hoffmann et al.

[11] Patent Number: 5,491,216
[45] Date of Patent: Feb. 13, 1996

[54] TRI-ARGININE INSULINS

[75] Inventors: James A. Hoffmann, Greenwood; Peter K. Lambooy, Indianapolis, both of Ind.

[73] Assignee: Eli Lilly and Company, Indianapolis, Ind.

[21] Appl. No.: 87,831

[22] Filed: Jul. 6, 1993

Related U.S. Application Data

[62] Division of Ser. No. 801,163, Nov. 26, 1991, abandoned.

[51] Int. Cl.$^6$ ............................ A61K 38/28; C07K 14/62
[52] U.S. Cl. ............................................. 530/303; 530/324
[58] Field of Search ...................... 530/303, 324; 514/3

[56] References Cited

U.S. PATENT DOCUMENTS

| | | | |
|---|---|---|---|
| 4,569,791 | 2/1986 | Frank et al. | 260/112.5 R |
| 4,569,792 | 2/1986 | Frank et al. | 260/112.5 R |
| 4,581,165 | 4/1986 | Frank et al. | 260/112.5 R |
| 4,608,364 | 8/1986 | Grau | 514/4 |
| 4,701,440 | 10/1987 | Grau | 514/3 |
| 4,992,418 | 2/1991 | Katsoyannis et al. | 514/3 |
| 5,008,241 | 4/1991 | Markussen et al. | 514/3 |
| 5,130,236 | 7/1992 | Hoffmann | 435/68.1 |

FOREIGN PATENT DOCUMENTS

| | | |
|---|---|---|
| 0264250 | 10/1987 | European Pat. Off. . |
| 0347781 | 6/1989 | European Pat. Off. . |
| 0427162A1 | 11/1990 | European Pat. Off. . |
| WO90/19299 | 10/1990 | WIPO . |
| 90/11299 | 10/1990 | WIPO . |

OTHER PUBLICATIONS

Receptor Binding and Biological Potency of Several Split Forms (Conversion Intermeidates) of Human Proinsulin, The Journal of Biological Chemistry, vol. 260, No. 26, Issue of Nov. 15, pp. 13989–13994, 1985.

Biochemical and Clinical Implications of Proinsilin Conversion Intermediates, B. D. Given, et al., J. Clin. Invest., vol. 76, 1398–1405, Oct. 1985.

Soluble, prolonged–acting insulin derivatives. I. Degree of protration and crystallizability of insulins substituted in the termini of the B–chain, J. Markussen, et al., Protein Engineering, vol. 1, No. 3, pp. 205–213, 1987.

Soluble, prolonged–acting insulin derivatives. II. Degree of protraction and crystallizability of insulins substituted in position A17, B8, B13, B27 and B30, J. Markussen, et al., Protein Engineering, vol. 1, No. 3, pp. 215–223, 1987.

Soluble, prolonged–acting insulin derivatives. III. Degree of protraction and crystallizability of insulins substituted in position A17, B8, B13, B27 and B30, J. Markussen, et al., Protein Engineering, vol. 2, No. 2, pp. 157–166, 1988.

In vitro activity of biosynthetic human diarginylinsulin, X. Zeuzem, et al., Diabetologia 33:65–71, 1990.

U.S. Ser. No. 07/447,486, Hoffmann, filed Dec. 7, 1989.

*Primary Examiner*—Jill Warden
*Assistant Examiner*—Benet Prickril
*Attorney, Agent, or Firm*—Ronald S. Maciak; David E. Boone

[57] ABSTRACT

This invention relates to human insulin analogs (tri-arg insulins) and includes two enzymatic methods for producing tri-arg insulins. These compounds can be formulated as a soluble entity up to pH 6.1 and have prolonged hypoglycemic activity. Tri-arg insulins have the basic structure of natural human insulin plus three additional arginine residues. Two of the three additional Arg residues are located in tandem at the carboxy terminus of the insulin B-chain, and the third Arg residue is located at the amino terminus of the insulin A-chain. Tri-arg insulin analogs, having certain amino acid substitutions at the B3, B10 and A21 positions, are within the instant invention.

4 Claims, 2 Drawing Sheets

TRI-ARGININE INSULINS

This application is a division, of application Ser. No. 07/801,163, filed Nov. 26, 1991, now abandoned.

TECHNICAL FIELD OF INVENTION

This invention belongs to the field of clinical medicine and provides a new form of insulin useful for the treatment of diabetes.

BACKGROUND OF THE INVENTION

A major part of diabetes therapy today involves treatment with intermediate and long-acting insulin products. These formulations are designed to control the patient's glucose levels during overnight time periods as well as provide one injection a day therapy in many patients.

A common feature of all these formulations is the fact that they are insoluble suspensions of insulin. Because of this, injection quantities can vary widely and glucose control after subcutaneous injection can be compromised (Skyler, J. S., *Medical Clinics of North America*, 72, 1337–1354 (1988)). Many of these formulations also require the addition of substantial amounts of protamine to provide long time action. Protamine is a fish protein which has been shown to cause antibody formation in some patients (Ellerhorst, J. A., et al., *The American Journal of the Medical Sciences*, 299, 298–301 (1987)).

With the advent of recombinant DNA technology, numerous analogs of insulin have been synthesized that can remain completely soluble in the formulation and yet have either quicker or more prolonged time action than natural insulin (Markussen, J., et al., *Protein Engineering*, 1, 215–223 (1987)). A most promising approach for the longer-acting insulin analogs is to formulate them to be completely soluble at a low pH (pH 3–4). After subcutaneous injection, the quick adjustment to the natural pH of the body environment (pH 7.4) causes these analogs to precipitate or crystallize. Their slow redissolution at pH 7.4 provides the time delay in action that is desired.

Two problems in this approach are as follow. First, the chronic administration of very acidic solutions may cause pain, skin necrosis and sloughing (DeLuca, P. P. and Rapp, R. P. *Pharmaceutics and Pharmacy Practice*; Banker, G. S. and Chalmers, R. K. Eds.; 238–278 (1982), J. B. Lippencott Co., Philadelphia, Pa.). Solutions closer to neutrality (pH 6–7) would clearly be more desirable in this regard. Second, since insulin analogs are unnatural to the body and as such may be recognized as non-self, antibodies to these insulin analogs may develop which can interfere with the patient's insulin therapy or cause other problems (Patterson, R., et al., *Annals of Allergy*, 64, 459–462 (1990)). Minimizing variations in a such a protein's structure could avoid this potential problem.

One insulin analog with intermediate time action and favorable solubility characteristics at pH 4–5 has already been described, namely di-arginine insulin (Zeuzem, S., et al., *Diabetologia*, 33, 65–71 (1990)). Di-arginine insulin however lacks one of the advantages of the present invention, that being solubility near pH 6. The present invention also shows superior time action characteristics over di-arginine insulin.

In addition to the physiological problem noted earlier with very acidic formulations, natural insulin-like molecules have another problem at low pH. Under acidic conditions, the asparagine residue in the number 21 position of the A-chain (A21) is very prone to deamidation and other side reactions that can lead to undesirable dimer and polymer formation (Markussen, J., et al., *Protein Engineering*, 2, 157–166 (1988)). These reactions proceed best below pH 4 and are almost nonexistent above pH 5 (Id.). Therefore, it would be most desirable in terms of human therapy to have an insulin-like molecule that possessed a prolonged hypoglycemic effect, low immunogenicity, and formulation solubility above pH 6.

This invention is based on the discovery that certain types of insulin analogs, herein referred to as tri-arginine (tri-arg) insulin and tri-arg insulin analogs, having the natural structure of insulin plus three additional arginine residues, have prolonged hypoglycemic activity in an animal model and can be formulated as a solution up to pH 6.1.

SUMMARY OF THE INVENTION

This invention is directed to compounds having the formula:

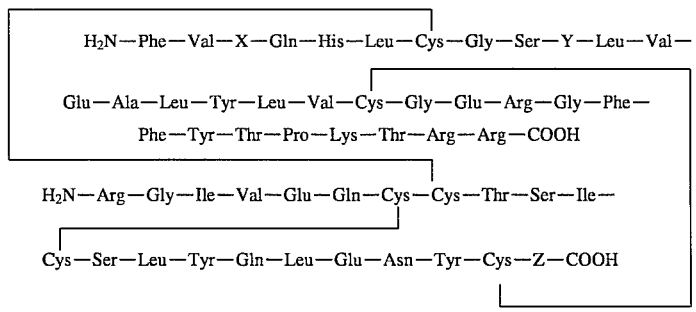

in which X and Z are selected from the group consisting of Ala, Arg, Asx, Cys, Glx, Gly, His, Ile, Leu, Lys, Met, Phe, Pro, Ser, Thr, Trp, Tyr or Val, and Y is selected from the group consisting of His, Asp or Glu, or pharmaceutically acceptable non-toxic salts thereof. The most preferred compounds are those which contain the naturally-occurring amino acids at the variable positions, namely wherein X is Asn, Y is His, and Z is Asn.

This invention also includes split (64) proinsulin-tri-arg-analogs consisting of human proinsulin wherein the number 3 residue of the B-chain (B3) and the number 21 residue of the A-chain (A21) are selected from the group consisting of Ala, Arg, Asx, Cys, Glx, Gly, His, Ile, Leu, Lys, Met, Phe, Pro, Ser, Thr, Trp, Tyr or Val, the number 10 residue of the B-chain (B10) is selected from the group consisting of His, Asp or Glu, and wherein the amide bond (peptide bond) between the number 64 residue of the C-peptide (Lys-64)

and the number 65 residue of the C-peptide (Arg 65) is broken, or a pharmaceutically acceptable salt thereof.

In a further embodiment, the invention encompasses des(64) proinsulin-tri-arg analogs consisting of split(64) proinsulin-tri-arg-analogs wherein Lys-64 is removed, or a pharmaceutically acceptable salt thereof. The most preferred compounds are those which contain the naturally-occurring amino acids at the variable positions, namely wherein the B3 and A21 residues are Asn and the B10 residue is His.

Another embodiment of the invention is a method for making human tri-arg insulin, comprising;

a) contacting human proinsulin with trypsin and carboxypeptidase B yielding des(64) human proinsulin;

b) isolating des(64) human proinsulin;

c) contacting des(64) human proinsulin with trypsin, and;

d) isolating tri-arg insulin.

Yet another embodiment of this invention is a method for making human tri-arg insulin, comprising;

a) contacting human proinsulin with a lysine endopeptidase under conditions that preferentially break the peptide bond between Lys-64 and Arg-65 of human proinsulin yielding split(64) human proinsulin;

b) isolating split(64) human proinsulin;

c) contacting split(64) human proinsulin with trypsin, and;

d) isolating human tri-arg insulin.

BREIF DESCRIPTION OF THE INVENTION

FIG. 1 illustrates the primary amino acid sequence of tri-arg insulin and tri-arg insulin analogs and shows the three disulfide linkages. The numbers under each residue correspond to that residue's position in the sequence starting at the amino terminus. The designation X in the number 3 position of the B-chain represents any one of the 20 naturally-occurring amino acids. The designation Y in the number 10 position of the B-chain represents His, Asp or Glu, and the designation Z at the A-chain carboxy terminus represents any one of the 20 naturally-occurring amino acids.

FIG. 2 shows the primary amino acid sequence of human proinsulin. The residues shown in black depict natural human insulin, and the residues shown in white depict the connecting peptide (C-peptide) of natural human proinsulin.

DETAILED DESCRIPTION OF THE INVENTION

For purposes Of this document, the 20 L-amino acids commonly found in naturally-occurring proteins will be abreviated using the standard three letter abreviations found in volume 37 of the *Code of Federal Regulations* § 1.822. Also for purposes of this document, a number of terms will be used according to the following definitions.

Figure 1:
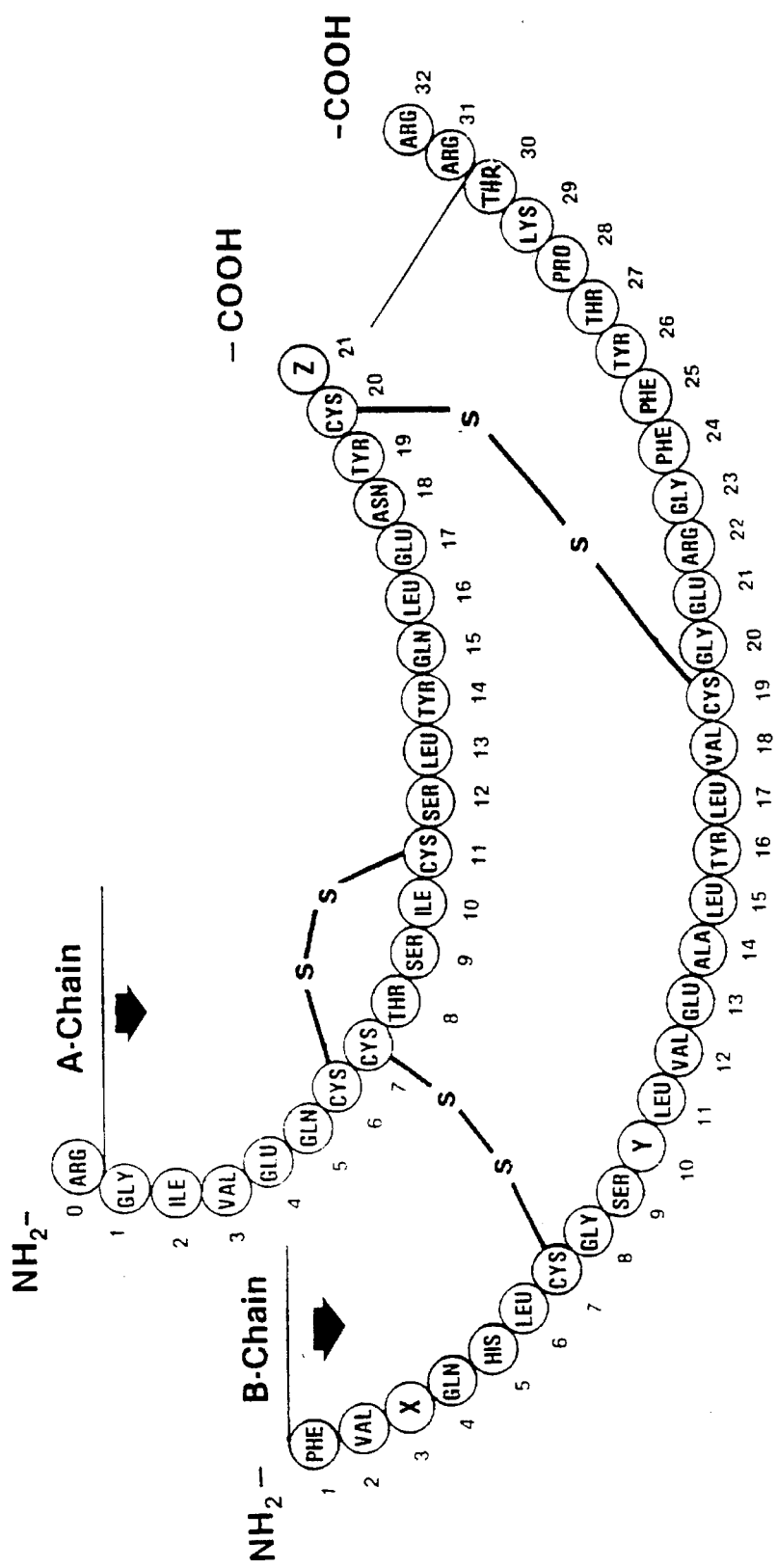
Figure 2:
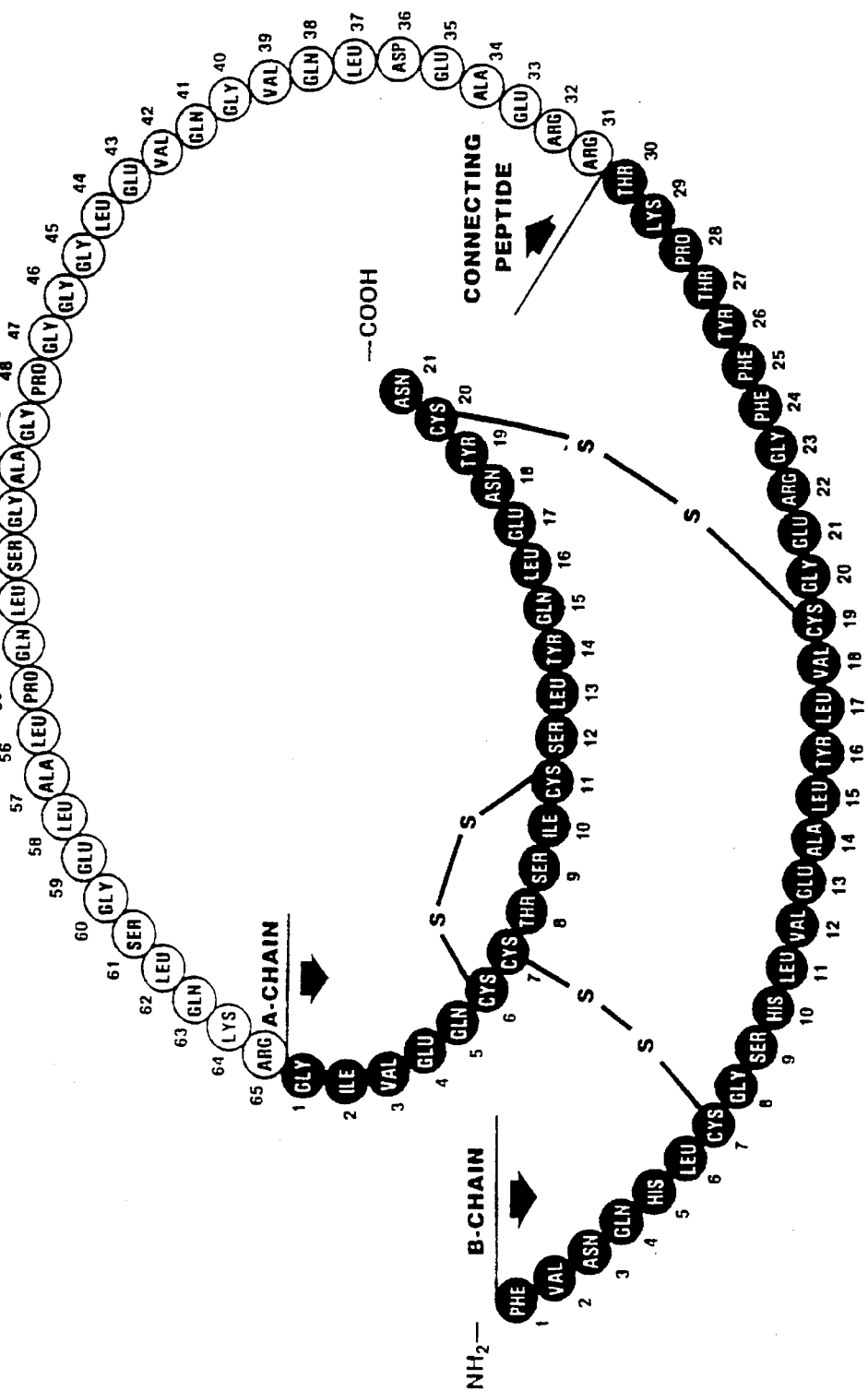

The term "tri-arg insulin" is defined as human insulin having two additional arginine residues at the carboxy terminus of the B-chain (Arg-31 and Arg-32 as shown in FIGS. 1 and 2) and one additional arginine residue at the amino terminus of the A-chain (Arg-0, A-chain as shown in FIG. 1 or Arg-65 as shown in FIG. 2).

The term "tri-arg insulin analog" is defined as tri-arg insulin wherein any one of the 20 naturally-occurring amino acids are substituted at either or both of the B3 or A21 positions, and wherein His, Asp or Glu may be substituted at the B10 position.

The term "proinsulin-tri-arg analog" means human proinsulin containing any of the possible B3, B10, and A21 substitutions consistent with this invention.

The term "split(64) proinsulin" is defined as human proinsulin wherein the peptide bond between Lys-64 and Arg-65 (Arg-0, A-chain) is broken (see FIGS. 1 and 2).

The term "split(64) proinsulin-tri-arg analog" is defined as split(64) proinsulin wherein one or more amino acid substitution consistent with this invention is made at the B3, B10, or A21 positions.

The term "des(64) proinsulin" is defined as split(64) proinsulin wherein Lys-64 is removed (see FIGS. 1 and 2).

The term "des(64) proinsulin-tri-arg analog" is defined as a des(64) proinsulin wherein one or more amino acid substitution consistent with this invention is made at the B3, B10, or A21 positions.

The term "pharmaceutically acceptable non-toxic acid addition salts" encompasses both organic and inorganic acid addition salts including, for example, those prepared from acids such as hydrochloric, sulfuric, sulfonic, tartaric, fumaric, hydrobromic, glycolic, citric, maleic, phosphoric, succinic, acetic, nitric, benozic, ascorbic, p-toluenesulfonic, benzenesulfonic, naphthalenesulfonic, propionic, carbonic, and the like, or salts, such as, for example, ammonium bicarbonate. Preferably, the acid addition salts are those prepared from hydrochloric acid, acetic acid, or carbonic acid. Any of the above salts can be prepared by conventional methods.

The term "carboxylic acid salts" includes, for example, zinc, ammonium, alkali metal salts such as sodium, magnesium, potassium, and lithium, and the like. Preferred carboxylic acid salts are the zinc and sodium salts.

The present invention relates to a number of human insulin analogs and methods for making them from proinsulin and proinsulin-tri-arg analogs. The general structure of the compounds falling within the scope of this invention is shown in FIG. 1, and the amino acid sequences are listed in SEQ ID NOS: 1–4. Included in the compounds of this invention are their pharmaceutically acceptable non-toxic acid addition salts and their pharmaceutically acceptable non-toxic carboxylic acid salts.

An essential feature which confers several unexpected and beneficial properties on the compounds of this invention is the presence of three additional arginine residues. Two of these residues are found at the carboxy terminus of the B-chain (Arg-31 and Arg-32 as shown in FIGS. 1 and 2), and the third additional arginine residue is located at the amino terminus of the A-chain (Arg-0, A-chain as shown in FIG. 1 or Arg-65 as shown in FIG. 2). These three arginine residues are present in the structure of natural human proinsulin but are not present in naturally occurring human insulin (see FIG. 2).

It is known that the number 3 position of the insulin B-chain (B3) may be substituted with other naturally-occurring amino acids without adversely affecting insulin structure or abolishing its biological activity. Therefore, any naturally-occurring amino acid at this position is consistent with the invention. However, to decrease the possibility of immunogenicity, Asn is preferred because Asn occupies the position in native insulin.

The above also holds true for the carboxy terminal residue of the A-chain (A21). Thus, any naturally-occurring amino acid at the A21 position is consistent with the invention. However, to decrease the possibility of immunogenicity, Asn is preferred because Asn occupies the A21 position in native insulin.

The third site at which amino acid substitutions may occur is the number 10 position of the B-chain (B10). Insulin analogs containing either Glu or Asp at the B10 position have been reported in the literature and have demonstrated increased potency (Burke, G. T., et al., *Biochemical and Biophysical Research Communications*, 173, 982–937 (1990)). Therefore, it is contemplated that Glu, Asp and His may occupy the B10 position in the instant invention. However, to decrease the possibility of immunogenicity, His is preferred because His occupies the B10 position in native insulin.

As is true for natural human insulin, tri-arg insulin and tri-arg insulin analogs require three disulfide bonds for proper quaternary structure. Two disulfide bonds bridge the A and B chains (A7-B7 and A20-B19), and one intrachain disulfide bond forms in the A chain (A6–A11) as is indicated in FIG. 1.

Tri-arg insulin and tri-arg insulin analogs can be prepared in a number of ways using well-known protein chemistry and recombinant DNA methods. The following illustrative list briefly outlines several basic ways to synthesize tri-arg insulin and tri-arg insulin analogs. The list is not meant to be exhaustive as many other variations of the basic schemes are possible.

1) Treatment of human proinsulin with trypsin and carboxypeptidase B, as described in Example 1.

2) Selective cleavage of human proinsulin between the Lys-64 and Arg-65 residues by lysine-cleaving endopeptidase, followed by mild trypsin cleavage at the preferred Arg-32 Glu-33 peptide bond as described in Example 2.

3) Recombinant DNA synthesis of Arg-0, A-chain and Arg-31,32 B-chain, followed by their combination via known disulfide chemistry. See U.S. Pat. No. 4,421,685, incorporated herein by reference, for details of such disulfide chemistry.

4) Chemical synthesis of Arg-0, A-chain and Arg-31,32 B-chain, followed by their combination via known disulfide chemistry.

5) Preparation by rDNA technology of a single chain mini-proinsulin molecule consisting of the peptide sequence B-chain - Arg-31 - Arg-32 - Arg-33 - A-chain. After disulfide formation, trypsin-like enzymes selectively, or with some preference, cleave the peptide bond between Arg 32 and Arg 33, yielding tri-arg insulin.

6) A mini-proinsulin molecule of the structure X -B-chain - Arg - Arg - Y - Arg - A-chain wherein X and Y are any naturally-occurring amino acids other than Arg or Lys. The mini-proinsulin is made by rDNA technology and is properly folded in the correct disulfide arrangement. Cleavage of this single chain peptide by trypsin is expected to occur first between Arg - Y. Subsequent removal of both X and Y from the amino termini of the B and A-chains, respectively, by the Edman procedure generates tri-arg insulin.

Each of the above schemes is subject to a wide variety of minor changes. Most notable are those involving all of the possible amino acid substitutions at the B3, B10, and A21 positions.

For example, method 1 can be altered by first synthesizing a human proinsulin-tri-arg analog either chemically or recombinantly. By mixing and matching all of the possible amino acid substitutions at each of the three positions, close to 1200 different proinsulin-tri-arg analogs are possible from which a tri-arg insulin analog can be produced using method 1.

As another example, method 1 can be altered by first making a B-chain-encoding DNA compound having a leader sequence. Following translation, the resulting peptide leader sequence can be enzymatically cleaved and the method completed as described. Other variations of this method encompass adding trailing sequences that result in clearable peptides yielding tri-arg insulin or a tri-arg insulin analogs.

The current state of the art in molecular biology readily provides the means for substituting any given amino acid in a protein sequence for another. Using well known techniques such as site specific mutagenesis, proinsulini-encoding DNA sequences can be altered at will, giving rise to the amino acid substitution of choice. Thus, the current state of the art enables practioners to make proinsulin-tri-arg analogs. Method 1 can then be used to make tri-arg insulin analogs containing any one or more of the amino acid substitutions encompassed by the invention.

Another means is also available for accomplishing the desired amino acid substitutions at the three variable positions. The state of the art in synthetic peptide chemistry provides methods, such as the Merrifield technique, for synthesizing peptides of at least 32 residues from single amino acids. Therefore, using method 3 outlined above, insulin A and B-chains can be synthesized to contain any of the possible amino acid substitutions at the variable positions.

Processes and intermediates used to make tri-arg insulin and tri-arg insulin analogs are further embodiments of the invention. Through the action of acetylated trypsin and carboxypetidase B, the process described in Example 1 generates des(64) proinsulin as an intermediate, though des(64) proinsulin has been found to have hypoglycemic activity of its own. The process described in Example 1 can also produce a des(64) proinsulin-tri-arg analog intermediate starting from the corresponding proinsulin-tri-arg analog.

The process described in Example 2 produces split(64) proinsulin as an intermediate by treating human proinsulin with a lysine endopeptidase. The process can also produce a split(64) proinsulin-tri-arg analog intermediate starting from the corresponding proinsulin-tri-arg analog. Split(64) proinsulin has also been found to have hypoglycemic activity of its own.

Endopeptidase-Lys-C is a lysine endopeptidase which is commercially available from a variety of sources, e.g., *Lysobacter enzymogenes* (Boehringer-Mannheim; Indianapolis, Ind.), *Pseudomonas aeruginosa* (Promega; Madison, Wis.) and *Achromobacter lyticus* (Wako Pure Chemical; Dallas, Tex.). It cleaves specifically at the carboxy terminus of lysine residues. To generate superior yields of split(64) proinsulin from proinsulin, preferential cleavage at the carboxy terminus of the Lys-64 position before cleavage at the carboxy terminus of the Lys-29 position is necessary. To this end, it has been found that Endopeptidase-Lys-C from *Pseudomonas aeruginosa* is a preferred source, and the enzyme from *Lysobacter enzymogenes* is the most preferred source.

The following examples are useful for understanding the invention and how it can be made. These examples are for illustrative purposes only and are not meant to limit the invention in any way.

EXAMPLE 1

Preparation of Tri-Arg-Insulin via the des (64) Human Proinsulin Intermediate

Recombinant human proinsulin prepared in E. coli was treated with porcine carboxypeptidase B (Promega; Madison, Wis.) and acetylated bovine trypsin (as prepared in European *J. Biochem.*, 2, 215–223 (1967)) at enzyme:substrate ratios by weight of approximately 1:1000 and 1:20,000, respectively, in 20 mM glycine buffer at pH 8. The reaction was allowed to proceed for approximately 27 hours at 8° C. and terminated by the addition of one volume of 7 M urea. The resulting solution was then charged onto a column of Q-Sepharose Fast Flow™ resin pre-equilibrated in 7 M urea, 10 mM Tris (tris(hydroxymethyl)aminomethane; Sigma; St. Louis, Mo.), 1 mM potassium tetrathionate at pH 8.1. The column was washed with the same buffer containing 25 mM sodium chloride and then eluted with a linear gradient from 25–65 mM sodium chloride in the equilibration buffer. Eluant fractions were collected and titrated to approximately pH 4.0 using glacial acetic acid immediately after collection.

Fractions which contained des(64) proinsulin, as determined by analytical HPLC, were pooled and concentrated using an Amicon S1Y3 spiral wound cartridge (Amicon; Danvers, Mass.). The retentate was diafiltered against 1 M acetic acid at approximately pH 2.5 at about 5° C. The resulting solution was diluted with an equal volume of water, filtered through a 0.2 micron filter and lyophilized under vacuum to dryness.

At ambient temperature, 2.91 gm of des(64) human proinsulin was dissolved in 291 ml of 0.05M Tris buffer containing 0.02 M $CaCl_2$ adjusted to pH 8 with 1N HCl. This solution was then cooled to 5° C. Approximately 364 μl of pork trypsin (Sigma; St. Louis, Mo.) at 1 mg/ml in water was added, resulting in an enzyme:substrate ratio by weight of 1:8000. After mixing, the solution was stored at 5° C.

The reaction was stopped after 4.5 hours by adding 10 ml of 1N HCl. The entire, clear solution was pumped onto a 5.5×30 cm C-18 Vydac™ HPLC column. After washing with water, the protein was eluted at 2.5 ml/min in a 22.5–42.5% acetonitrile gradient in 0.5% trifluoroacetic acid (TFA) buffer over 24 hours. The eluant was monitored by absorbance at 276 nm. 20 ml fractions were collected, and several fractions were examined analytically by HPLC using a C-8 Zorbax™ column in an acetonitrile gradient in 0.1M sodium monobasic phosphate pH 2.1 buffer.

The tri-arg insulin containing fractions (116–128) were pooled and lyophilized to yield 0.94 g of product, HPLC purity 87%. The structure of this product was verified by amino acid composition, N-terminal sequencing analysis and fast atom bombardment mass spectroscopy (FAB-MS).

EXAMPLE 2

Preparation of Tri-arg Insulin via the Split(64) Human Proinsulin Intermediate

Human proinsulin (800 mg) was dissolved in 80 ml of a pH 7.7 buffer containing 25 mM Tris and 1 mM EDTA. *Pseudomonas aeruginosa* Endopeptidase-Lys-C (Promega; Madison, Wis.) was prepared at 0.1 mg/ml in the same buffer, and 200 μl was added to the proinsulin solution, resulting in a enzyme:substrate ratio by weight of 1:40,000. The reaction solution was mixed well, then incubated for 9.5 hours at 37° C. The solution was acidified to pH 3.0 by adding 1N HCl, then placed on a 5.5×30 cm Vydac™ C-18 preparative HPLC column equilibrated in 0.5% TFA. The purified protein was eluted over a 20 hour period using a gradient containing 0–40% acetonitrile in the TFA buffer. The fractions corresponding to split(64) proinsulin were pooled and lyophilized yielding 237 mg of product. The identity of this product was verified by amino acid analysis, FAB-MS and N-terminal sequencing analysis.

A portion of the split(64) proinsulin was prepared at 1 mg/ml in the 25 mM Tris, 1 mM EDTA buffer at pH 7.7 and beef trypsin (Sigma; St. Louis, Mo.) was prepared at 0.1 mg/ml in the same buffer. To a 700 μl volume of the split(64) proinsulin was added 7 μl of the trypsin solution, resulting in an enzyme:substrate ratio by weight of 1:1,000. The reaction was stirred at ambient temperature for 30 minutes. HPLC analysis of the reaction products was then performed on a 4.6×250 mm Zorbax™ C-8 column in a shallow acetonitrile gradient in 0.1M sodium phosphate pH 2.1 buffer. The analysis showed that essentially all of the split(64) proinsulin was digested and the predominant product was tri-arg insulin.

EXAMPLE 3

Preparation of Asp(A21)-Tri-arg Insulin Analog

Tri-arg insulin (40 mg), as prepared in Example 1, was dissolved in 4 ml of 0.01N HCl and stored at ambient temperature for 12 days. The solution was then incubated as 37° C. for an additional 16 days. The main component in the final solution was purified by preparative HPLC. Five portions of the solution (0.5–1.0 ml each) were injected onto a 21.5×250 mm zorbax™ C-8 HPLC column equilibrated in 0.1M sodium sulfate pH 2.3 buffer containing 26% acetonitrile. The sample components were eluted from a gradient of 26–30% acetonitrile in sodium sulfate buffer. The eluate fractions containing the main component from all five runs were combined, diluted with an equal volume of water and desalted on a C-18 Sep-Pak™ cartridge (Millipore; Bedford, Mass.). The purified peptide was eluted and concentrated in 50% acetonitrile and 50% TFA (0.5%) buffer and lyophilized. The structure of the purified product was verified by amino acid analysis, FAB-MS and HPLC analysis of the individual A and B-chains. Analytical HPLC showed a 95% purity of Asp(A21)-tri-arg insulin analog.

EXAMPLE 4

Biological Activity of Tri-Arg-Insulins

Two to four ml volumes of 40 U/ml tri-arg insulin solutions were prepared in 0.05M sodium acetate buffer at a final protein concentration of approximately 2.0 mg/ml. Solutions were prepared containing various amounts of zinc (0–2.4 mg/ml) in the form of zinc chloride. Glacial acetic acid was used to solubilze each of the solutions at a final pH range of pH 4–6. Based on an estimated 70% biopotency relative to human insulin (insulin receptor binding) and a standardized value of 28.85 U/mg for human insulin, the following formula was used in the preparation of the test solutions.

2 mg/ml×28.85 U/mg protein×70% potency=40 U/ml.

New Zealand White rabbits, mostly female, all weighing 0 2.7–4 kg, 0.5–4 years of age and fasted 16 hours prior to administration of sample were used for testing. Forty U/ml solutions of tri-arg insulin, Asp(21)-tri-arg insulin analog, split(64) proinsulin (pH 7.35), des(64) proinsulin (pH 7.46), di-arg insulin (prepared according to Zeuzem, et al., *Diabetologia*, 33, 65–71, (1990)), Humulin L™ (Lente human insulin, intermediate time action; Eli Lilly & Co.; Indianapolis, Ind.) or Humulin U™ (Ultralente human insulin, long time action; Eli Lilly & Co.; Indianapolis, Ind.) were each injected into 10 rabbits subcutaneously at the back of the neck at a dose of 0.2 U/kg.

At various times, 100 μl volumes of blood were obtained from the marginal ear veins, mixed with 900 μl volumes of anticoagulant (EDTA-sodium fluoride) and analyzed for glucose content. The glucose values were standardized to reflect percent of original blood glucose measured prior to sample injection. The results are shown in Table 1.

TABLE 1

| Insulin | Added Zinc mg/ml | Percent of Original Blood Glucose n = 10 Hours after Sample Injection | | | |
|---|---|---|---|---|---|
| | | 1 | 2 | 4 | 6 |
| Humulin L | 0 | 58.2 | 48.0 | 90.6 | 96.2 |
| Humulin U | 0 | 53.4 | 55.3 | 85.3 | 92.5 |
| Tri-Arg | 0 | 51.1 | 56.0 | 86.9 | 95.3 |
| Asp(A21)-Tri-Arg | 0 | 67.4 | 84.2 | 94.8 | 89.8 |
| Des(64) HPI | 0 | 63.1 | 70.5 | 90.6 | 90.0 |
| Split(64) HPI | 0 | 61.7 | 83.8 | 94.8 | 94.1 |
| Di-Arg | 0 | 60.6 | 85.4 | 98.1 | 99.8 |
| Tri-Arg | 0.014 | 43.3 | 50.3 | 90.5 | 94.9 |
| Tri-Arg | 0.05 | 51.4 | 57.7 | 88.2 | 95.1 |
| Tri-Arg | 0.14 | 61.6 | 52.1 | 76.1 | 96.5 |
| Tri-Arg | 0.33 | 76.2 | 67.7 | 88.5 | 91.9 |
| Tri-Arg | 0.5 | 71.8 | 65.0 | 88.4 | 86.9 |
| Tri-Arg | 1.4 | 83.7 | 71.1 | 75.3 | 91.4 |
| Tri-Arg | 2.4 | 79.2 | 71.1 | 74.5 | 70.1 |
| Asp(A12)-Tri-Arg | 2.4 | 84.2 | 70.3 | 84.4 | 91.9 |
| Di-Arg | 2.4 | 76.3 | 73.4 | 95.5 | 96.7 |

EXAMPLE 5

Percent solubility of tri-arg insulin was compared to that of di-arg insulin based on optical density (O.D.) at 276 nm wavelength. One mg/ml solutions of tri-arg insulin (as prepared in Example 1) or di-arg insulin (prepared according to Zeuzem, et al., *Diabetologia*, 33, 65–71, (1990)) were prepared in 2 mM borate-citrate-glycine buffer at pH 9.5. Samples of each solution were adjusted to various pH levels by the dropwise addition of either 5N HCl or 5N NaOH and measured using a digital pH meter. Each sample was then centrifuged for 30 minutes at approximately 10,000 rpm. The supernatants were then removed and the O.D. for each was measured at 276 nm using a spectrophotometer. Concentrations were calculated from the O.D. values using 0.98 as the expected value for a 1 mg/ml solution. Percent soluble material was calculated by dividing the concentration after centrifugation by the original concentration. The results are shown in Table 2.

TABLE 2

| Di-Arg Insulin | | Tri-Arg Insulin | |
|---|---|---|---|
| pH | Percent Soluble | pH | Percent Soluble |
| 3.46 | 95.2 | — | — |
| 4.08 | 82.9 | — | — |
| 4.51 | 73.0 | 4.94 | 87.4 |
| 5.56 | 19.0 | 5.56 | 53.8 |
| 5.93 | 8.1 | 5.92 | 25.3 |
| 6.47 | 10.1 | 6.56 | 10.5 |
| 7.02 | 22.2 | 6.99 | 9.1 |
| 7.54 | 44.4 | 7.53 | 10.7 |
| 8.06 | 102.0 | 8.05 | 21.2 |

These data show tri-arg insulin has a higher solubility at the desirable formulation pH (pH 5–6) but also a lower solubility at the physiologic pH after subcutaneous injection (pH 7.4). Hence, tri-arg insulins can be formulated at a higher and more preferrable pH than di-arg insulins. Therefore, the solubility characteristics of tri-arg insulins after subcutaneous injection are expected to prolong the time action relative to di-arg insulin.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 32 amino acids
      ( B ) TYPE: amino acid
      ( C ) STRANDEDNESS: single
      ( D ) TOPOLOGY: linear ( i i ) MOLECULE TYPE: protein ( i x ) FEATURE:
      ( A ) NAME/KEY: Cross-links
      ( B ) LOCATION: 7..8
      ( D ) OTHER INFORMATION: /label=Cross-Linkage
        / note="Cys7 of this sequence (the B-chain of tri-Arg- insulin) is disulfide linked to Cys8 of the A-chain of tri-Arg-insulin."

( i x ) FEATURE:
      ( A ) NAME/KEY: Cross-links
      ( B ) LOCATION: 19..20
      ( D ) OTHER INFORMATION: /label=Cros-linkage
        / note="The Cys19 of this sequence (the B-chain of tri-Arg- insulin) is disulfide linked to Cys21 of tri-Arg- insulin."

( x i ) SEQUENCE DESCRIPTION: SEQ ID NO:1:

```
Phe Val Xaa Gln His Leu Cys Gly Ser His Leu Val Glu Ala Leu Tyr
1                5                   10                  15
Leu Val Cys Gly Glu Arg Gly Phe Phe Tyr Thr Pro Lys Thr Arg Arg
            20              25                  30
```

( 2 ) INFORMATION FOR SEQ ID NO:2:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Cross-links
        ( B ) LOCATION: 7..8
        ( D ) OTHER INFORMATION: /label=Cross-Linkage
             / note="Cys7 of this sequence (the B-chain of
             tri-Arg- insulin) is disulfide bonded to Cys8 of
             the A-chain of tri-Arg-insulin."

( i x ) FEATURE:
        ( A ) NAME/KEY: Cross-links
        ( B ) LOCATION: 19..20
        ( D ) OTHER INFORMATION: /label=Cross-Linkage
             / note="Cys19 of this sequence (the B-chain of
             tri-Arg- insulin) is disulfide bonded to Cys21 of
             the A-chain of tri-Arg-insulin."

( x i ) SEQUENCE DESCRIPTION: SEQ ID NO:2:

```
Phe Val Xaa Gln His Leu Cys Gly Ser Asp Leu Val Glu Ala Leu Tyr
1                5                   10                  15
Leu Val Cys Gly Glu Arg Gly Phe Phe Tyr Thr Pro Lys Thr Arg Arg
            20              25                  30
```

( 2 ) INFORMATION FOR SEQ ID NO:3:

( i ) SEQUENCE CHARACTERISTICS:
        ( A ) LENGTH: 32 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Cross-links
        ( B ) LOCATION: 7..8
        ( D ) OTHER INFORMATION: /label=Cross-linkage
             / note="Cys7 of this sequence (the B-chain of
             Tri-ARg- insulin) is disulfide bonded to Cys8 of
             the A-chain of tri-Arg-insulin."

( i x ) FEATURE:
        ( A ) NAME/KEY: Cross-links
        ( B ) LOCATION: 19..20
        ( D ) OTHER INFORMATION: /label=Cross-Linkage
             / note="Cys19 of this sequence (the B-chain of
             tri-Arg- insulin) is disulfide bonded to Cys21 of
             the A-chain of tri-Arg-insulin."

( x i ) SEQUENCE DESCRIPTION: SEQ ID NO:3:

```
Phe Val Xaa Gln His Leu Cys Gly Ser Glu Leu Val Glu Ala Leu Tyr
1                5                   10                  15
Leu Val Cys Gly Glu Arg Gly Phe Phe Thr Tyr Pro Lys Thr Arg Arg
            20              25                  30
```

( 2 ) INFORMATION FOR SEQ ID NO:4:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: protein ( i x ) FEATURE:
        ( A ) NAME/KEY: Disulfide-bond
        ( B ) LOCATION: 7..12

( i x ) FEATURE:
        ( A ) NAME/KEY: Cross-links
        ( B ) LOCATION: 8..9
        ( D ) OTHER INFORMATION: /label=Cross-Linkage
            / note="Cys8 of this sequence (the A-chain of
            tri-Arg- insulin) is disulfide bonded to Cys7 of
            the B-Chain of tri-Arg-insulin."

( i x ) FEATURE:
        ( A ) NAME/KEY: Cross-links
        ( B ) LOCATION: 21..22
        ( D ) OTHER INFORMATION: /label=Cross-linkage
            / note="Cys21 of this sequence (the A-chain of
            tri-Arg- insulin) is disulfide bonded to Cys19 of
            the B-chain of tri-Arg-insulin."

( x i ) SEQUENCE DESCRIPTION: SEQ ID NO:4:

Arg Gly Ile Val Glu Gln Cys Cys Thr Ser Ile Cys Ser Leu Tyr Gln
1               5                   10                  15

Leu Glu Asn Tyr Cys Xaa
                20

We claim:

1. Split(64) proinsulin-tri-arg-analog consisting of human proinsulin wherein the B3 and A21 residues are selected from the group consisting of Ala, Arg, Asx, Cys, Glx, Gly, His, Ile, Leu, Lys, Met, Phe, Pro, Ser, Thr, Trp, Tyr or Val, the B10 residue is selected from the group consisting of His, Asp or Glu, and wherein the amide bond between Lys-64 and Arg-65 is broken, or a pharmaceutically acceptable salt thereof.

2. Split(64) proinsulin consisting of the compound of claim 1 wherein the B3 residue is Asn, the B10 residue is His, and the A21 residue is Asn, or a pharmaceutically acceptable salt thereof.

3. Des(64) proinsulin-tri-arg analog consisting of the compound of claim 1 wherein Lys-64 is removed, or a pharmaceutically acceptable salt thereof.

4. Des(64) proinsulin consisting of the compound of claim 3 wherein the B3 residue is Asn, the B10 residue is His, and the A21 residue is Asn, or a pharmaceutically acceptable salt thereof.

* * * * *